US012420031B2

(12) United States Patent
Chen

(10) Patent No.: US 12,420,031 B2
(45) Date of Patent: Sep. 23, 2025

(54) ASSEMBLY, CASSETTE AND MEDICAMENT DELIVERY DEVICE

(71) Applicant: SHL MEDICAL AG, Zug (CH)

(72) Inventor: Hsueh-Yi Chen, New Taipei (TW)

(73) Assignee: SHL Medical AG, Zug (CH)

( * ) Notice: Subject to any disclaimer, the term of this patent is extended or adjusted under 35 U.S.C. 154(b) by 761 days.

(21) Appl. No.: 17/774,932

(22) PCT Filed: Nov. 11, 2020

(86) PCT No.: PCT/EP2020/081708
§ 371 (c)(1),
(2) Date: May 6, 2022

(87) PCT Pub. No.: WO2021/115706
PCT Pub. Date: Jun. 17, 2021

(65) Prior Publication Data
US 2022/0387730 A1    Dec. 8, 2022

(30) Foreign Application Priority Data

Dec. 9, 2019   (EP) .................................... 19214361

(51) Int. Cl.
*A61M 5/32*   (2006.01)
*A61M 5/24*   (2006.01)

(52) U.S. Cl.
CPC ..... *A61M 5/326* (2013.01); *A61M 2005/2407* (2013.01); *A61M 2005/244* (2013.01); *A61M 2005/2485* (2013.01); *A61M 2205/12* (2013.01)

(58) Field of Classification Search
CPC ............ A61M 5/20; A61M 2005/2492; A61M 2005/2407; A61M 2005/2437;
(Continued)

(56) References Cited

U.S. PATENT DOCUMENTS

2015/0335829 A1* 11/2015 Giambattista ....... A61M 5/3146
604/192
2017/0258998 A1    9/2017 Stamp
(Continued)

FOREIGN PATENT DOCUMENTS

CN    109922848 A    6/2019
CN    110072572 A    7/2019
(Continued)

OTHER PUBLICATIONS

International Search Report and Written Opinion for Int. App. No. PCT/EP2020/081708, mailed Jan. 28, 2021.

*Primary Examiner* — Nilay J Shah
(74) *Attorney, Agent, or Firm* — McDonnell Boehnen & Berghoff LLP

(57) ABSTRACT

An assembly for receiving a medicament container having a container carrier extending along a longitudinal axis, the container carrier having a carrier body, and a flexible carrier arm extending from the carrier body substantially parallel with the longitudinal axis; and a rotator comprising a hollow rotator body and a through hole which extends substantially parallel with the longitudinal axis, wherein the container carrier is arranged to receive the rotator such that the carrier arm extends through the through hole, and wherein the rotator is arranged to rotate about the longitudinal axis and relative to the container carrier. A cassette and a medicament delivery device are also provided.

19 Claims, 11 Drawing Sheets

(58) Field of Classification Search
CPC .......... A61M 2005/244; A61M 5/3271; A61M 5/3272; A61M 2005/2485; A61M 5/24; A61M 2005/31518; A61M 5/3245
See application file for complete search history.

(56) References Cited

U.S. PATENT DOCUMENTS

| | | |
|---|---|---|
| 2017/0368259 A1 | 12/2017 | Olson et al. |
| 2019/0192776 A1 | 6/2019 | Alexandersson |

FOREIGN PATENT DOCUMENTS

| | | |
|---|---|---|
| TW | 201841664 A | 12/2018 |
| WO | 2014/095424 A1 | 6/2014 |
| WO | 2016/034407 A2 | 3/2016 |
| WO | 2018/192750 A1 | 10/2018 |

\* cited by examiner

ASSEMBLY, CASSETTE AND MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2020/081708 filed Nov. 11, 2020, which claims priority to European Patent Application No. 19214361.8 filed Dec. 9, 2019. The entire disclosure contents of these applications are herewith incorporated by reference into the present application.

TECHNICAL FIELD

The present disclosure generally relates to an assembly for a medicament container. In particular, an assembly for receiving a medicament container, a cassette for receiving a medicament container, and a medicament delivery device comprising a cassette, are provided.

BACKGROUND

A wide range of medicament delivery devices for self-administration of medicaments are known. Some medicament delivery devices have two parts interconnected for the use, such as a base unit and a cassette. The base unit usually comprises a resettable drive mechanism and can thus be reused for multiple injections. The cassette is often containing or receiving the medicament container with the medicament such as a syringe, a cartridge or the like, which then can be thrown away after the use of the medicament and substituted with a new one i.e. a disposable cassette.

The base unit and the cassette may be connected by the user, such as a patient, a medical care person. The connection can be made in various different ways known in the art. The user then presses a button on the base unit or presses the proximal end of the cassette against a delivery site in order to activate the drive mechanism and thereby trigger the medicament delivery. Thereafter, the cassette is then disconnected from the base unit in order to enable disposal of the cassette.

WO 2018/192750 discloses an administration assembly for a medicament delivery device, comprising: an elongated tubular delivery member cover, a cartridge holder having a cartridge blocking protrusion configured to prevent the medicament cartridge from moving proximally until being subjected to a proximally directed force, a needle assembly comprising a double-edged needle having a proximally extending needle portion and a distally extending needle portion, wherein the needle assembly is configured to be assembled with the cartridge holder so that the distally extending needle portion extends into the cartridge holder, and an administration mechanism including a plunger rod configured to be proximally biased, wherein the delivery member cover is configured to be linearly displaced in the distal direction relative to the cartridge holder, and wherein the delivery member cover is configured to activate the administration mechanism when moved in the distal direction, causing the administration mechanism to move the cartridge holder in the proximal direction and to subsequently move the plunger rod in the proximal direction inside the cartridge holder with a force larger than a threshold value.

US2017258998 A1 discloses an autoinjector comprising a housing in which a syringe barrel seat accommodates a syringe barrel containing a medicament and needle. The housing also provides an abutment surface which acts to support a front end of the syringe barrel ahead of a plunger during injection. The abutment surface may comprise flexible inwardly directed fingers.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

One object of the present disclosure is to provide an assembly for receiving a medicament container, which assembly is simple and/or enables simple operation.

A further object of the present disclosure is to provide an assembly for receiving a medicament container, which assembly is reliable and/or enables reliable operation.

A still further object of the present disclosure is to provide an assembly for receiving a medicament container, which assembly solves several or all of the foregoing objects in combination.

A still further object of the present disclosure is to provide a cassette for receiving a medicament container, which cassette solves one, several or all of the foregoing objects.

A still further object of the present disclosure is to provide a medicament delivery device comprising a cassette, which medicament delivery device solves one, several or all of the foregoing objects.

According to one aspect, there is provided an assembly for receiving a medicament container, the assembly comprising a container carrier extending along a longitudinal axis, the container carrier comprising a carrier body, and a flexible carrier arm extending from the carrier body substantially parallel with the longitudinal axis; and a rotator comprising a hollow rotator body and a through hole which extends substantially parallel with the longitudinal axis; wherein the container carrier is arranged to receive the rotator such that the carrier arm extends through the through hole; and wherein the rotator is arranged to rotate about the longitudinal axis and relative to the container carrier.

When the rotator rotates relative to the container carrier, the carrier arm moves within the through hole relative to the rotator. The through hole may be curved or arc-shaped and centered with respect to the longitudinal axis. The carrier arm may thus move within the through hole in a circumferential direction with respect to the longitudinal axis. The through hole may have an angular extension about the longitudinal axis of at least 30°, such as 70° to 110°, such as 90°.

The carrier arm may be configured to engage a flange of the medicament container in order to axially lock the medicament container to the assembly. The engagement may for example be a snap fit. The flange may for example be a distal flange, such as a finger flange or an annular flange, of the medicament container.

The medicament container may for example be a syringe or cartridge containing medicament. The assembly may be disposable. The assembly may further comprise a medicament container.

The through hole may be provided at a distal end of the rotator. A length of the carrier arm may thus be longer than a length of the rotator along the longitudinal axis. When the rotator is received by the container carrier, the rotator body may abut against the carrier body.

The container carrier may be arranged to receive the rotator such that the carrier arm extends radially outside the rotator body in a distal direction and through the through hole.

According to one example, the container carrier comprises two such flexible carrier arms, and the rotator comprises two such through holes. In this case, each carrier arm may be received through a respective through hole. The carrier arms may be arranged substantially opposing, or opposing, with respect to the longitudinal axis. Conversely, the through holes may be arranged substantially opposing, or opposing, with respect to the longitudinal axis.

The carrier arm may comprise an engaging arm structure arranged to resiliently engage a flange of the medicament container to thereby lock the medicament container along the longitudinal axis when the rotator is received by the container carrier and the medicament container is received by the assembly. When the engaging arm structure engages the flange, the rotator may be positioned between the carrier body and the engaging arm structure.

The engaging arm structure may be a recess, such as a radially inwardly directed recess. In case the container carrier comprises two or more flexible carrier arms, each engaging arm structure may be a recess.

According to a further aspect, there is provided a cassette for receiving a medicament container, the cassette comprising an assembly according to the present disclosure. The cassette may further comprise a medicament container.

The cassette may be disposable. Since the cassette comprises the assembly, the assembly may be referred to as a subassembly of the cassette.

The cassette may further comprise a housing configured to receive the assembly; a container cover for covering a proximal end of the medicament container when received in the assembly; and a biasing member arranged to bias the container cover relative to the housing in a proximal direction. The container cover may be arranged to be pressed directly against a dose delivery site of a user.

The biasing member may be a compression spring. The biasing member may be compressed between the container cover and the housing.

The proximal end of the medicament container is typically a needle. The container cover may thus be a needle cover.

The container cover may be axially movable and non-rotatable relative to the housing. Alternatively, or in addition, the rotator may be rotatable relative to the container cover.

The rotator may comprise an engageable rotator structure, and the container cover may comprise a cover structure engaging the rotator structure. In this case, the cover structure may be arranged to move from a first position of the rotator structure to a second position of the rotator structure in response to an axial movement of the container cover in a distal direction, and the cover structure may be arranged to move from the second position to a third position of the rotator structure in response to an axial movement of the container cover in a proximal direction.

When the cover structure moves from the first position to the second position of the rotator structure, the rotator may rotate about the longitudinal axis. When the cover structure moves from the second position to the third position of the rotator structure, the rotator may not rotate about the longitudinal axis.

When the cover structure adopts the first, second and third position, also the container cover adopts the first, second and third position, respectively, relative to the rotator. The proximal end of the medicament container may be covered by the container cover in each of the first position and the third position. The proximal end of the medicament container may be exposed by the container cover in the second position. The cover structure may be a pin. The rotator structure may be a track.

The rotator may comprise two such engageable rotator structures and the container cover may comprise two such engaging cover structures. The two rotator structures may be arranged substantially opposing, or opposing, with respect to the longitudinal axis. The two cover structures may be arranged substantially opposing, or opposing, with respect to the longitudinal axis.

The cover structure and the rotator structure may be arranged such that the container cover becomes locked to the rotator when the cover structure engages the third position of the rotator structure. In this way, the container cover can be locked to the rotator after medicament expulsion from the medicament container. As a consequence, the proximal end of the medicament container cannot be exposed by distal movement of the container cover a second time.

The rotator structure may comprise a flexible rotator arm arranged between the second position and the third position. The rotator arm may be arranged to deflect, e.g. radially inwards, from a neutral position when the cover structure moves along the rotator structure from the second position to the third position, and the rotator arm may be arranged to return to the neutral position when the cover structure has passed the rotator arm.

The cassette may further comprise a guide arrangement configured to guide the container carrier about the longitudinal axis with respect to the housing when the container carrier is inserted into the housing. The guide arrangement may for example comprise one or more carrier guide surfaces on the container carrier and one or more housing guide surfaces on the housing. The guide arrangement may be configured to guide the container carrier into a defined rotational relationship about the longitudinal axis with respect to the housing by relative movement of the container carrier and the housing along the longitudinal axis.

According to a further aspect, there is provided a medicament delivery device comprising a cassette according to the present disclosure. The medicament delivery device may be referred to as an "all in one" device. The medicament delivery device may further comprise a medicament container.

The medicament delivery device may further comprise a base unit having an electric drive arrangement and a switch for activating the drive arrangement. The cassette may be detachably attachable to the base unit, and may comprise a switch activation part arranged to activate the switch in response to an axial movement of the container cover in a distal direction when the cassette is attached to the base unit. The drive arrangement may be arranged to drive expulsion of medicament from the medicament container when the cassette is attached to the base unit and the switch is activated.

A cassette loaded with a medicament container can be attached to the base unit. A user may then grab the medicament delivery device and place the container cover onto a dose delivery site of the user. The user may then move the medicament delivery device proximally towards the dose delivery site such that the container cover moves distally relative to the remainder of the medicament delivery device. The distal movement of the container cover will both expose the proximal end of the medicament container (e.g. a needle of a syringe), and cause the switch activation part to activate the switch and thereby activate the drive arrangement to initiate expulsion of medicament from the medicament container into the dose delivery site. The medicament delivery device thus makes use of the container cover as a trigger for initiating medicament delivery into a user.

The base unit may be used multiple times. The base unit may further comprise an electric power source, such as a battery. In this case, the base unit may be referred to as a powerpack. The drive arrangement may for example comprise a battery, an electric motor, a chain drive and a plunger. The base unit may also comprise a further switch arranged to be activated when the cassette is attached to the base unit.

The switch activation part may be fixed with respect to the container cover. For example, the switch activation part may be an integral part of the container cover.

The switch activation part may be arranged to move in the distal direction in response to the movement of the container cover in the distal direction in order to activate the switch. Alternatively, or in addition, the switch activation part may be arranged to directly contact the switch in response to the distal movement of the container cover.

The switch may comprise a lever movable from a passive state to an active state by the switch activation part. The lever may for example be tilted between the passive state and the active state.

According to a further aspect, there is provided a medicament delivery device comprising a base unit having an electric drive arrangement and a switch for activating the drive arrangement; a cassette detachably attachable to the base unit, the cassette comprising a housing configured to receive a medicament container containing medicament, a container cover for covering a proximal end of the medicament container when received in the housing, and a switch activation part arranged to activate the switch in response to an axial movement of the container cover in a distal direction when the cassette is attached to the base unit; wherein the drive arrangement is arranged to drive expulsion of medicament from the medicament delivery member when the cassette is attached to the base unit and the switch is activated. One, several or each of the drive arrangement, the switch, the housing, the container cover and the switch activation part may be of any type according to the present disclosure. The cassette may further comprise a biasing member, such as a compression spring, arranged to force the container cover in the proximal direction relative to the housing.

The switch activation part may be fixed with respect to the delivery member cover. The switch activation part may be arranged to move in the distal direction in response to the movement of the container cover in the distal direction in order to activate the switch. The cassette may further comprise a rotator according to the present disclosure.

BRIEF DESCRIPTION OF THE DRAWINGS

Further details, advantages and aspects of the present disclosure will become apparent from the following embodiments taken in conjunction with the drawings, wherein.

DETAILED DESCRIPTION

Figure 1:
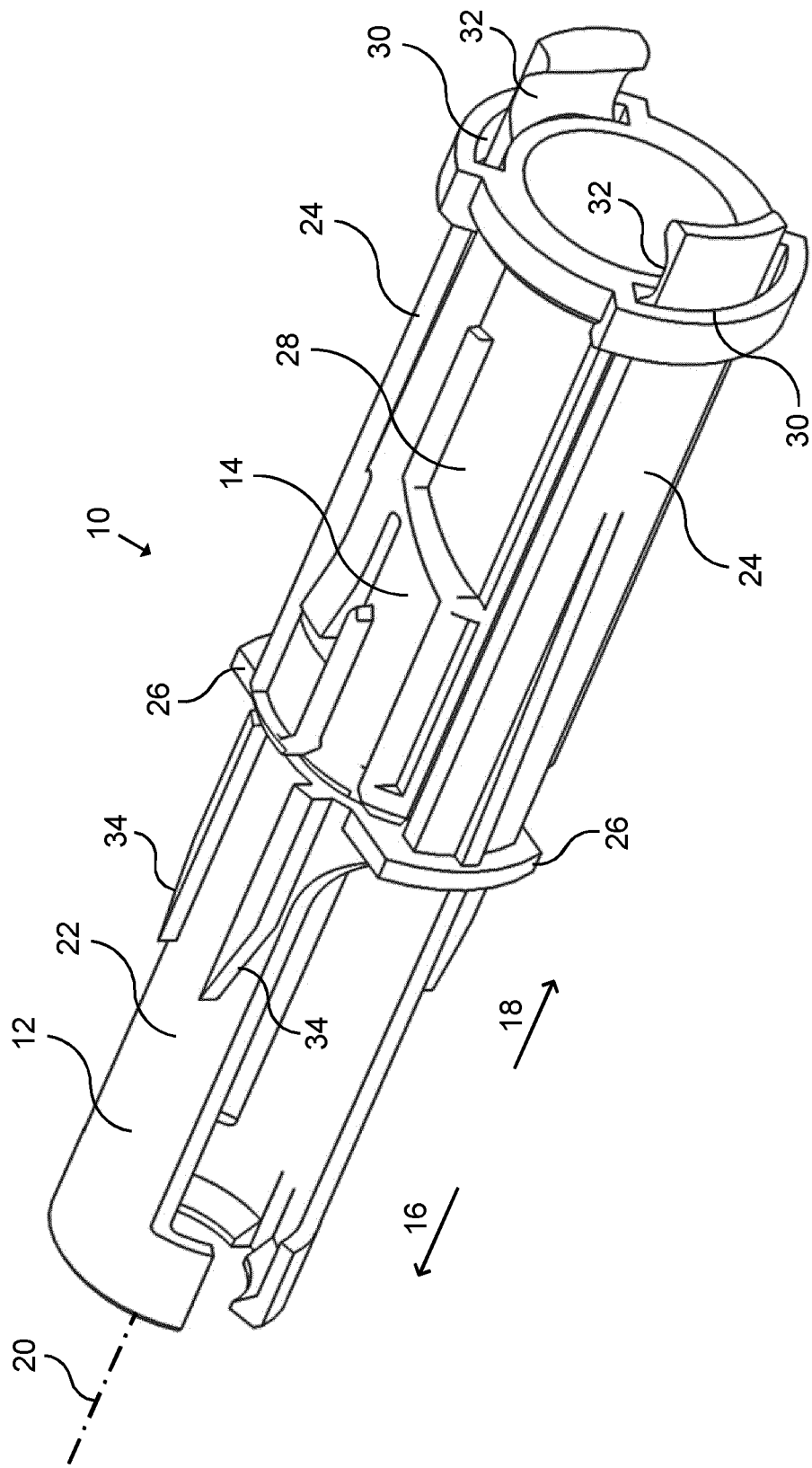
FIG. 1 schematically represents a perspective view of an assembly for receiving a medicament container.

In the following, an assembly for receiving a medicament container, a cassette for receiving a medicament container, and a medicament delivery device comprising a cassette, will be described. The same or similar reference numerals will be used to denote the same or similar structural features.

Figure 2:
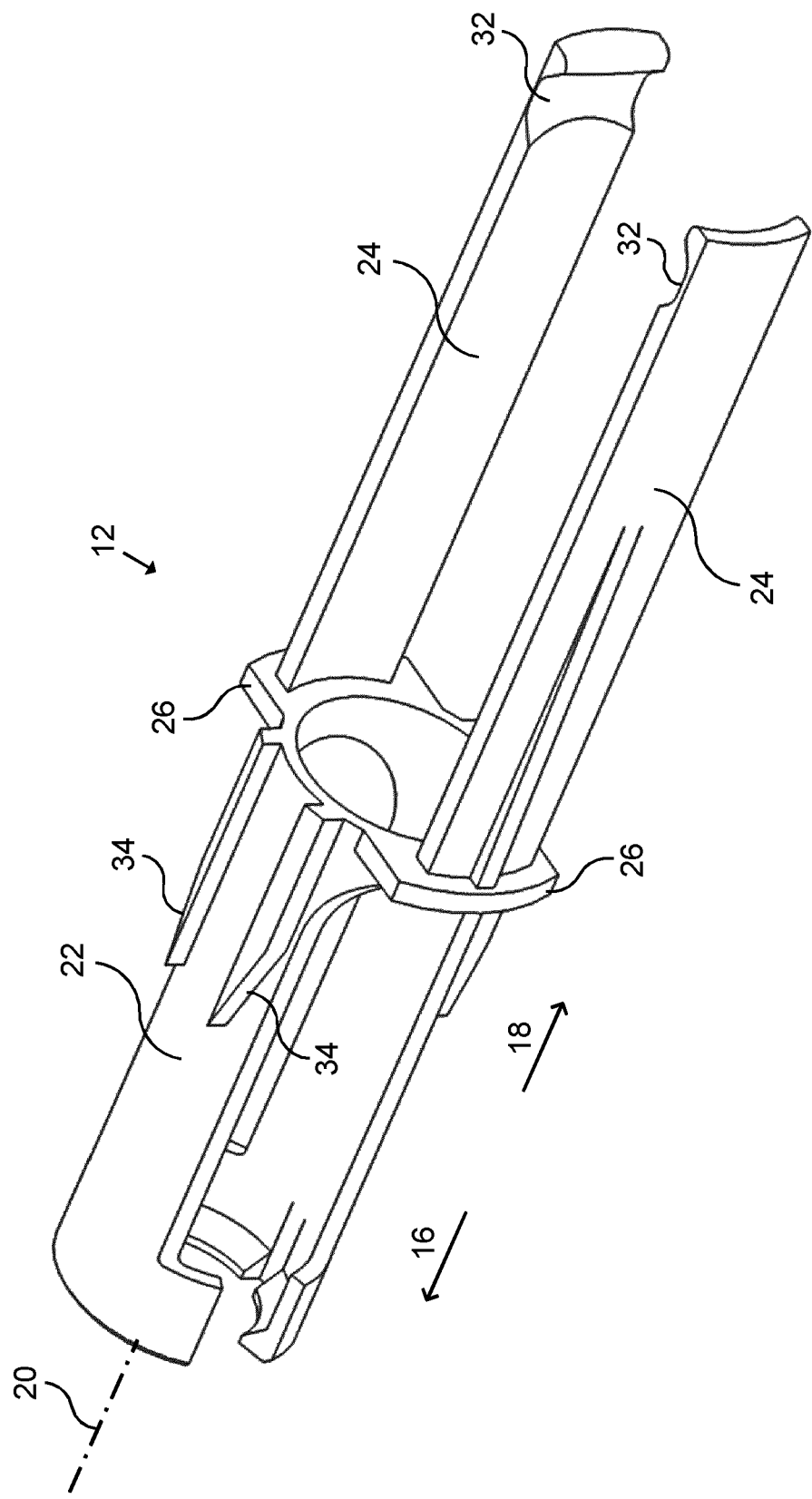
FIG. 2 schematically represents a perspective view of a container carrier of the assembly.

FIG. 1 schematically represents a perspective view of an assembly 10 for receiving a medicament container. The assembly 10 comprises a container carrier 12 and a rotator 14. FIG. 1 further denotes a proximal direction 16 and a distal direction 18. FIG. 2 schematically represents a perspective view of the container carrier 12 and FIG. 3 schematically represents a perspective view of the rotator 14.

Figure 3:
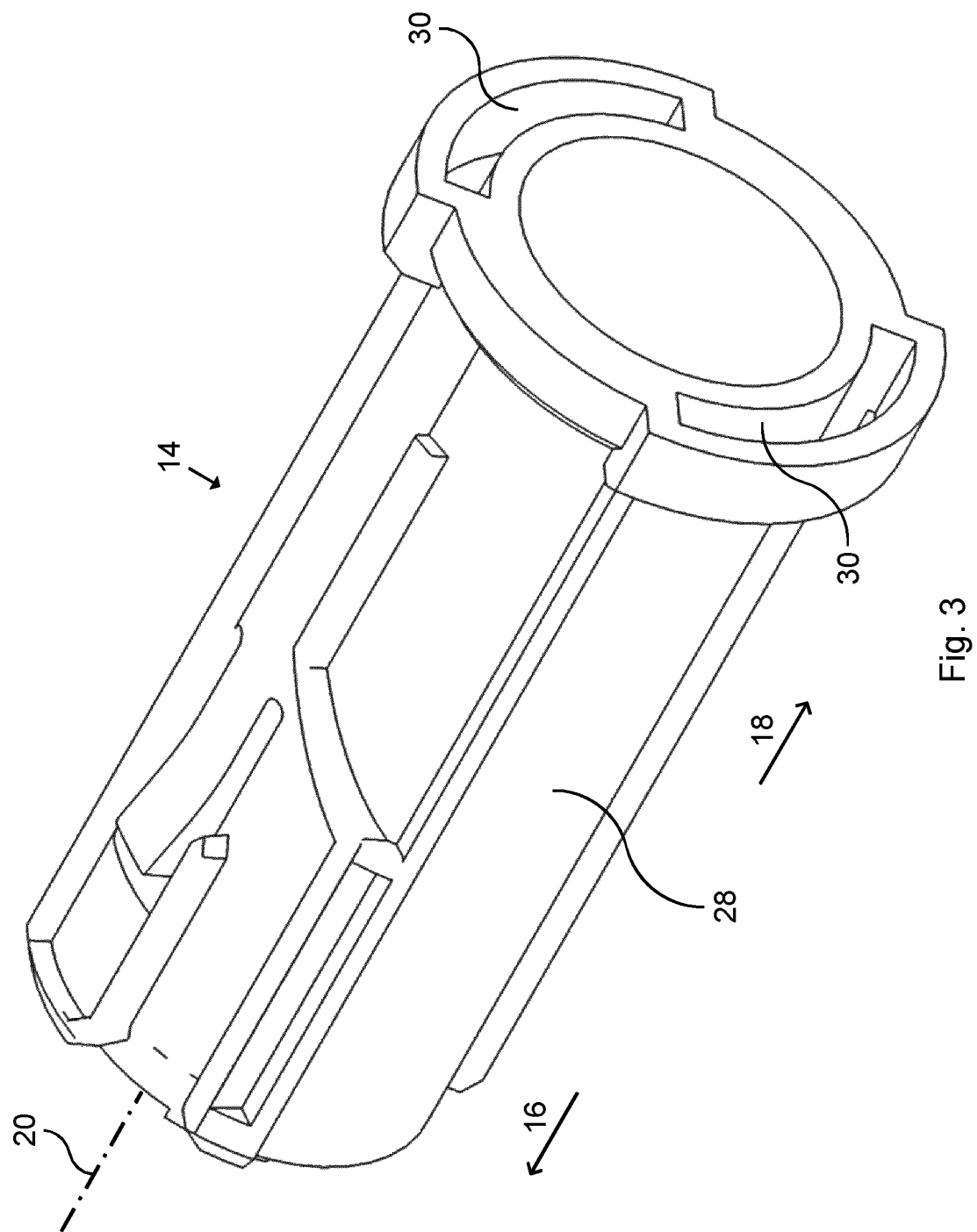
FIG. 3 schematically represents a perspective view of a rotator of the assembly.

With collective reference to FIGS. 1 to 3, the container carrier 12 extends along a longitudinal axis 20. The container carrier 12 comprises a carrier body 22. The carrier body 22 is hollow and concentric with respect to the longitudinal axis 20.

The container carrier 12 further comprises two flexible carrier arms 24. Although the container carrier 12 of this example comprises two carrier arms 24, the container carrier 12 may alternatively comprise only one carrier arm 24, or more than two carrier arms 24. The two carrier arms 24 have corresponding designs.

The container carrier 12 further comprises two protrusions 26. Each protrusion 26 protrudes radially outwards with respect to the longitudinal axis 20 and are oppositely arranged with respect to the longitudinal axis 20. The protrusions 26 are arranged at a distal end of the carrier body 22.

Each carrier arm 24 extends from the carrier body 22 in the distal direction 18 parallel with the longitudinal axis 20. The two carrier arms 24 are oppositely arranged with respect to the longitudinal axis 20.

The rotator 14 comprises a hollow rotator body 28 which is a tubular body having an inner and outer surface. The rotator body 28 of this example is cylindrical.

The rotator 14 further comprises two through holes 30. The number of through holes 30 corresponds to the number of carrier arms 24. The two through holes 30 have corresponding designs. Each through hole 30 extends substantially parallel with the longitudinal axis 20. Thus, each through hole 30 is open in a direction substantially parallel with the longitudinal axis 20.

The through holes 30 are arranged radially outside the rotator body 28, i.e. radially with respect to the longitudinal axis 20. Moreover, each through hole 30 is arranged at a distal end of the rotator body 28. In this example, each through hole 30 is arc-shaped and centered with respect to the longitudinal axis 20. An angular extension of each through hole 30 with respect to the longitudinal axis 20 is approximately 90°. Although the through holes 30 of this example are arranged radially outside the rotator body 28, it is also feasible that the through holes 30 extend axially with respect to the longitudinal axis 20 between the inner and the outer surface of the rotator.

The container carrier 12 is arranged to receive the rotator 14. When the rotator 14 is received by the container carrier 12, as shown in FIG. 1, each carrier arm 24 extends through a corresponding through hole 30. Thus, also the through holes 30 are oppositely arranged with respect to the longitudinal axis 20.

Each carrier arm 24 further comprises an engaging arm structure 32. Each engaging arm structure 32 is here exemplified as a radially inwardly facing (with respect to the longitudinal axis 20) recess. The engaging arm structures 32 are provided at a distal end of the respective carrier arm 24.

When the rotator 14 is received by the container carrier 12, a proximal facing annular surface of the rotator body 28 abuts against a distal facing surface of the carrier body 22 and the distal ends of the carrier arms 24 protrude distally from the through holes 30. Thereby, the engaging arm structures 32 are exposed. A length of each carrier arm 24 (along the longitudinal axis 20) is longer than a length of the rotator body 28 (which in this example is the same as a length of the rotator 14).

Furthermore, when the rotator 14 is received by the container carrier 12, the rotator 14 is allowed to rotate about the longitudinal axis 20 relative to the container carrier 12. In this example, the rotator 14 is allowed to rotate approximately 30° relative to the container carrier 12.

The container carrier 12 further comprises carrier guide surfaces 34. The carrier guide surfaces 34 of this example extend radially and at an angle to the longitudinal axis 20. The carrier guide surfaces 34 form part of one example of a guide arrangement as described herein.

Figure 4:
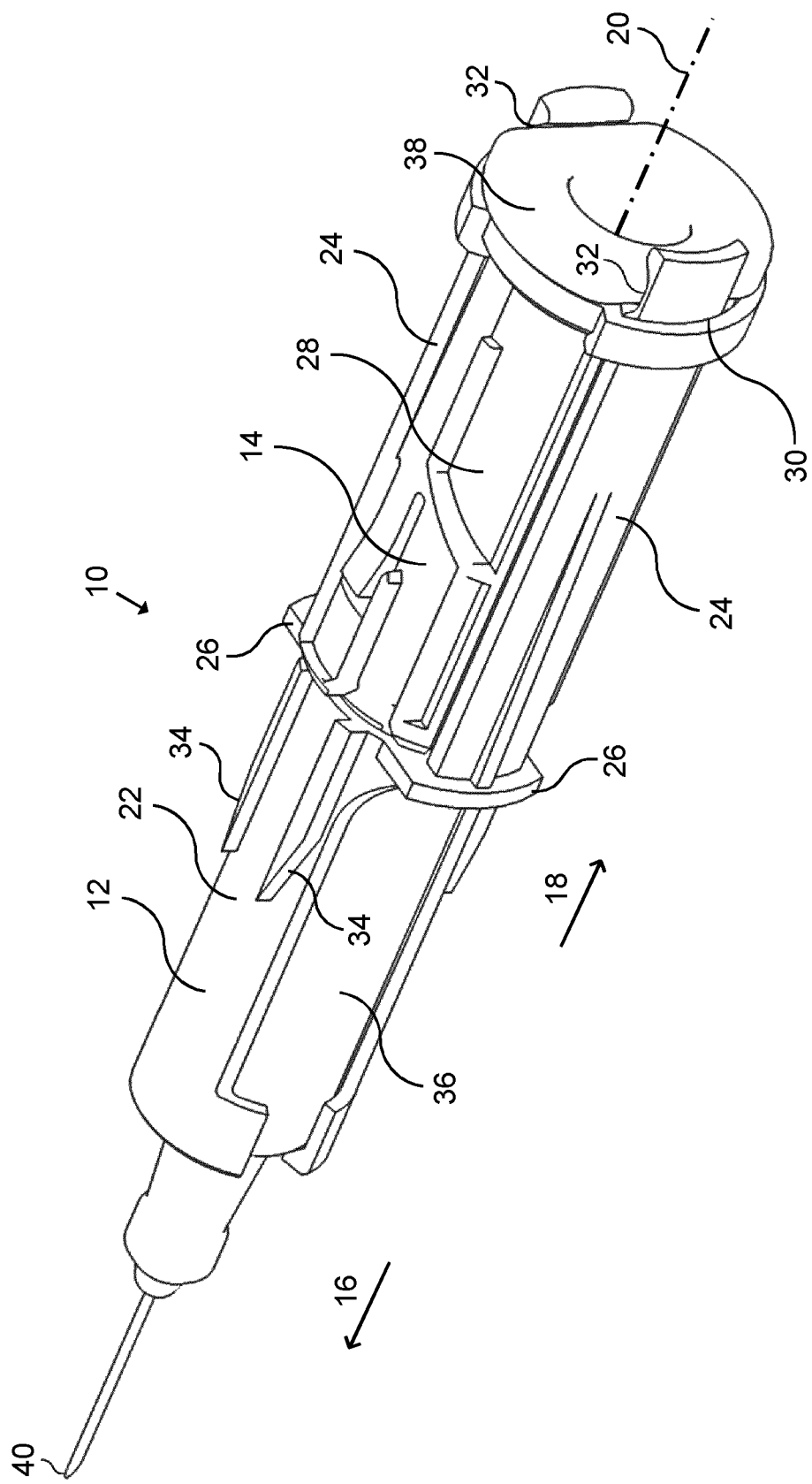
FIG. 4 schematically represents a perspective view of the assembly and a medicament container.

FIG. 4 schematically represents a perspective view of the assembly 10 and a medicament container 36 received in the assembly 10. The medicament container 36 contains medicament for being delivered e.g. injected into a user. The medicament container 36 of this example is a syringe comprising a distal flange 38 and a needle having a proximal end 40. The medicament container can also be a cartridge or any other type of medicament container known in the art.

During insertion of the medicament container 36 in the proximal direction 16 into the assembly 10, the flange 38 initially pushes a distal end of each carrier arm 24 radially outwards until the flange 38 becomes aligned with the engaging arm structures 32 along the longitudinal axis 20. At this position, the resiliency of the carrier arms 24 causes the engaging arm structures 32 to snap onto the flange 38 and resiliently engage the flange 38. The medicament container 36 is thereby locked relative to the assembly 10 and prevented from moving axially. When inserted into the assembly 10, the medicament container 36 is contained inside the carrier body 22 and inside the rotator body 28.

Figure 5:
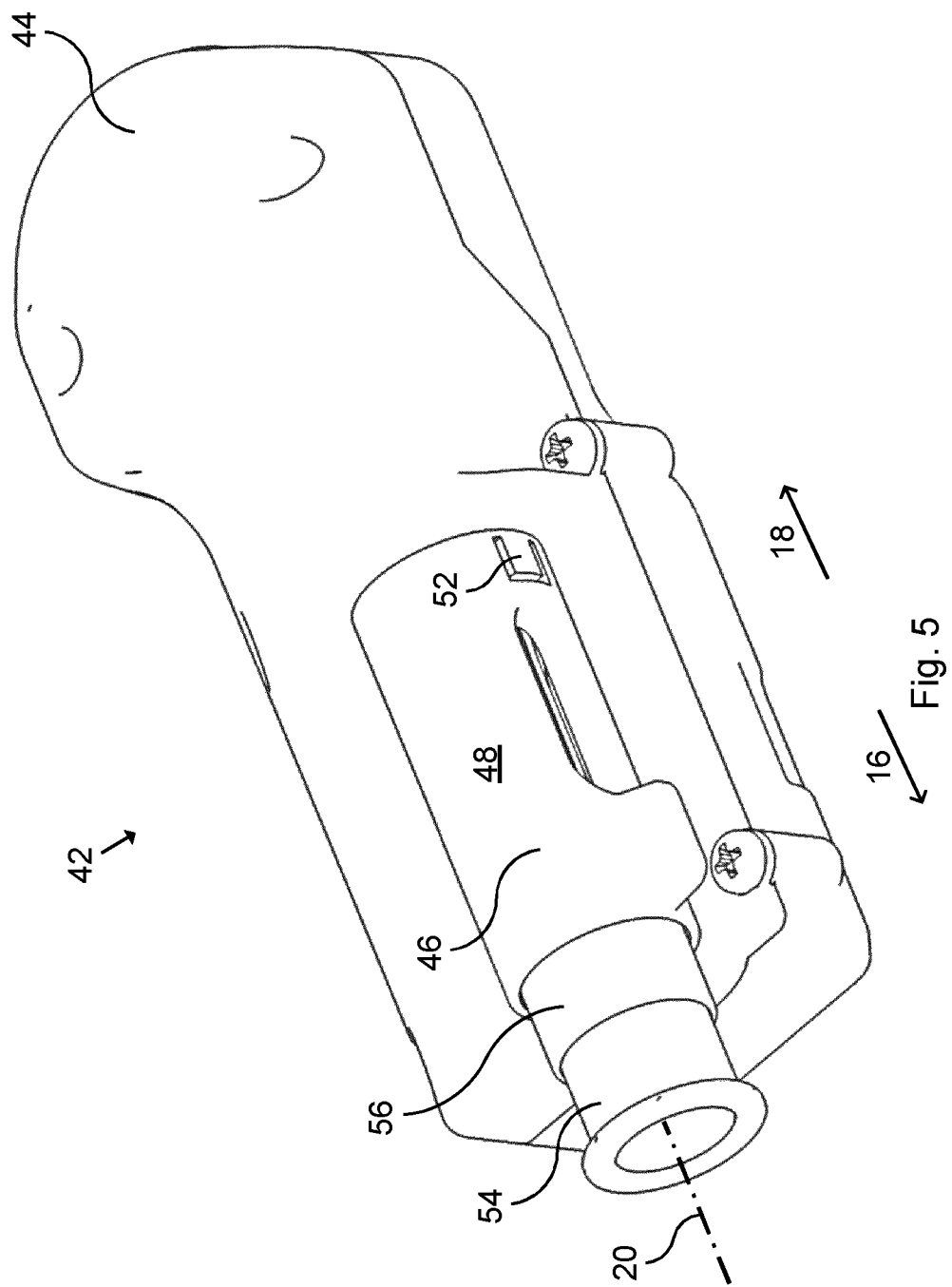
FIG. 5 schematically represents a perspective view of a medicament delivery device comprising the assembly.

FIG. 5 schematically represents a perspective view of a medicament delivery device 42. The medicament delivery device 42 comprises a base unit 44 and a cassette 46. The cassette 46 comprises the assembly 10.

The cassette 46 is detachably attachable to the base unit 44. FIG. 5 illustrates the cassette 46 attached to the base unit 44. The cassette 46 is disposable and the base unit 44 is designed for multiple use.

Figure 6:
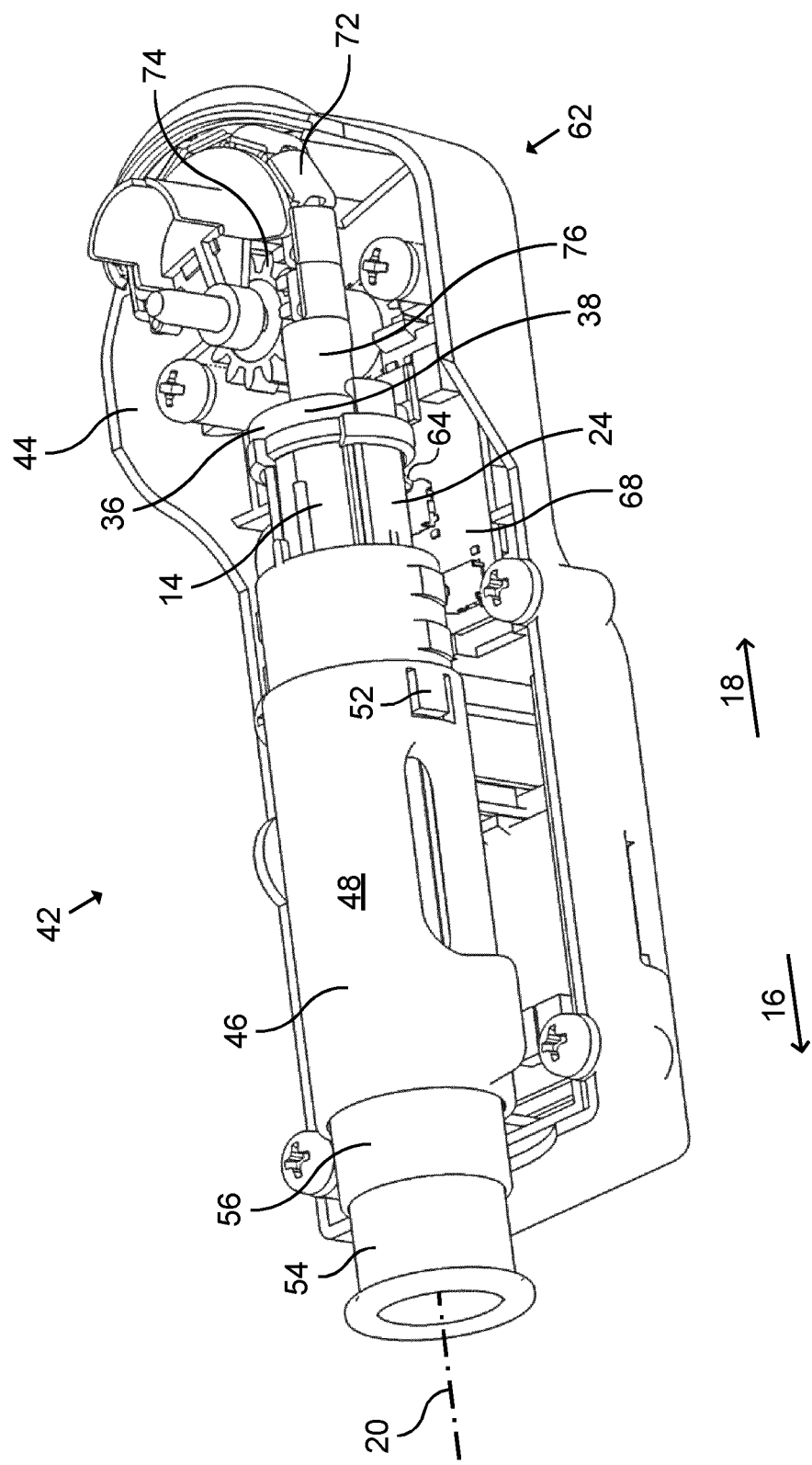
FIG. 6 schematically represents a partial perspective view of the medicament delivery device.
Figure 7:
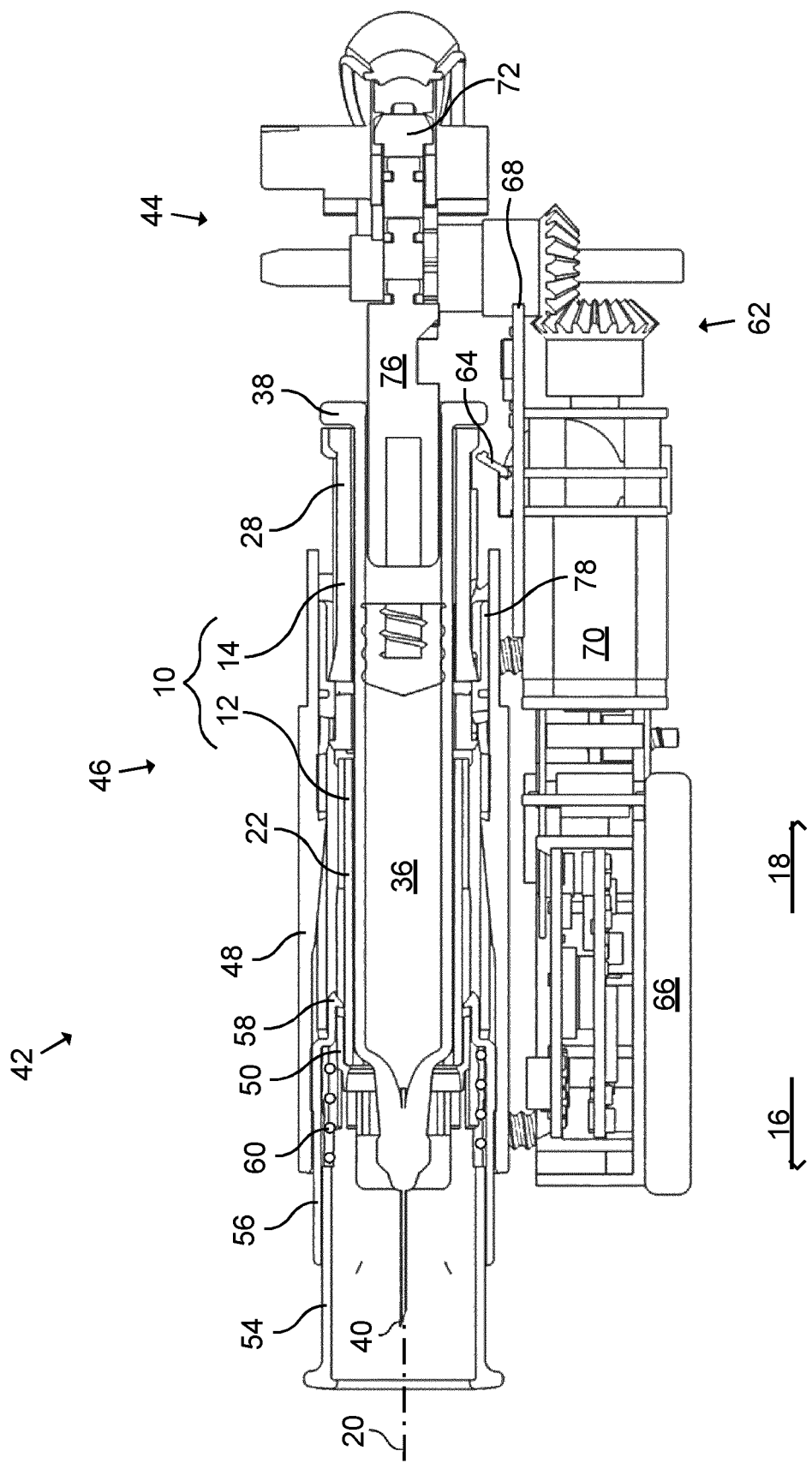
FIG. 7 schematically represents a partial cross-sectional side view of the medicament delivery device.
Figure 8:
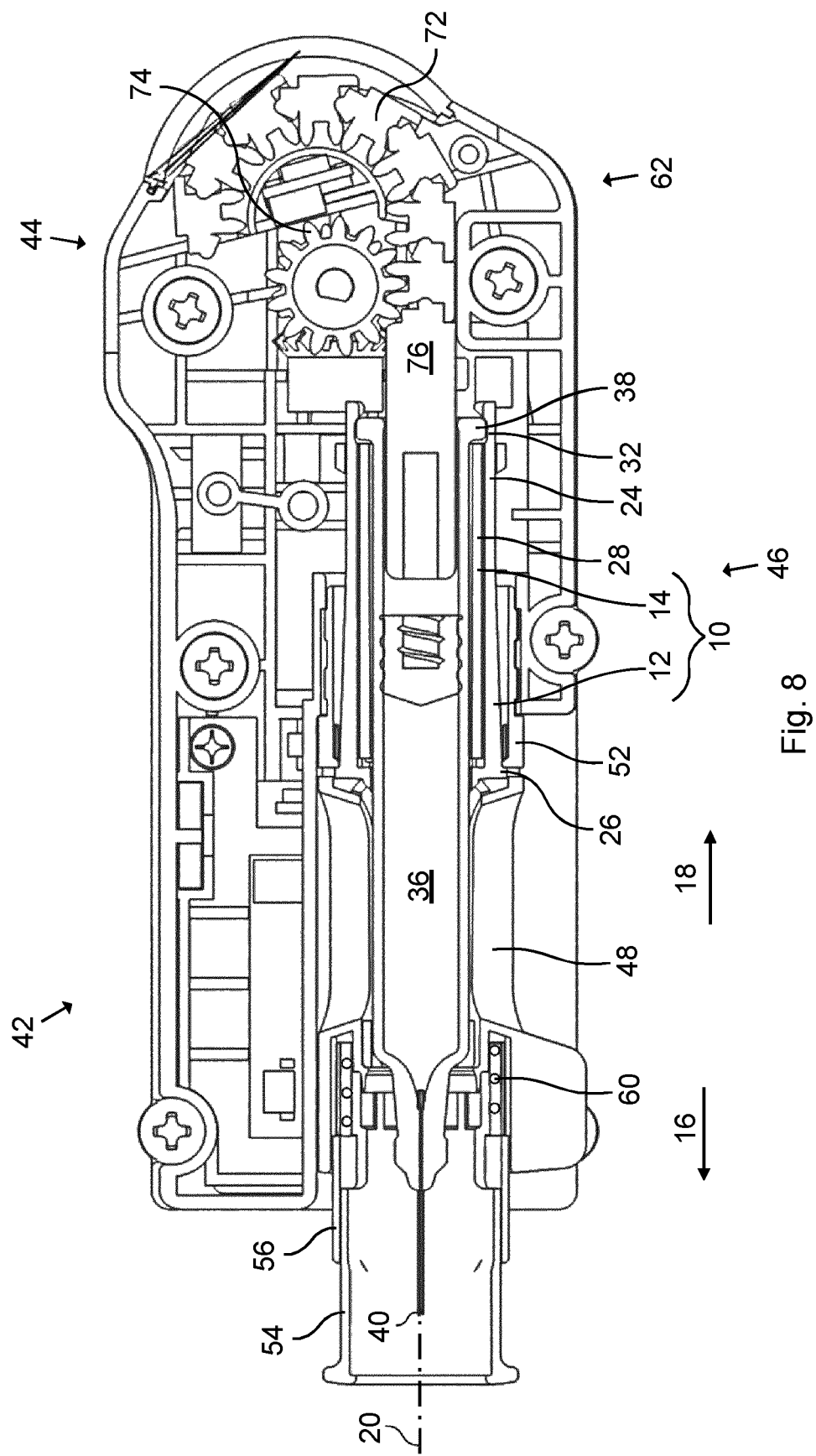
FIG. 8 schematically represents a partial cross-sectional top view of the medicament delivery device.

FIG. 6 schematically represents a partial perspective view of the medicament delivery device 42, FIG. 7 schematically represents a partial cross-sectional side view of the medicament delivery device 42, and FIG. 8 schematically represents a partial cross-sectional top view of the medicament delivery device 42.

With collective reference to FIGS. 5 to 8, the cassette 46 comprises a housing 48. The housing 48 is configured to receive the assembly 10. The housing 48 of this example is a tubular body, which is generally cylindrical and concentric with respect to the longitudinal axis 20. The housing 48 comprises an inner part 50, see FIG. 11.

The housing 48 further comprises two flexible members 52, here exemplified as tabs. Each flexible member 52 engages a respective protrusion 26 of the container carrier 12. Thus, by inserting the assembly 10 into the housing 48 in the proximal direction 16, the flexible members 52 snap over the protrusions 26. Thereby, the assembly 10 becomes axially locked to the housing 48.

The cassette 46 further comprises a container cover 54. The container cover 54 is movable along the longitudinal axis 20 relative to the housing 48 from the illustrated proximal position to a distal position (not illustrated). In the proximal position, the container cover 54 covers the proximal end 40 of the medicament container 36. The container cover 54 is concentric with respect to the longitudinal axis 20. Moreover, the container cover 54 is rotationally locked relative to the housing 48 about the longitudinal axis 20.

The cassette 46 of this example further comprises a biasing member cover 56. The biasing member cover 56 is generally cylindrical and concentric with respect to the longitudinal axis 20. The biasing member cover 56 is axially locked to the housing 48 by means of a radial step and hooks 58 engaging the inner part 50.

The cassette 46 further comprises a biasing member 60. In this example, the biasing member 60 is a compression coil spring concentric with respect to the longitudinal axis 20. The biasing member 60 is arranged radially inside the biasing member cover 56. The biasing member 60 is compressed between the container cover 54 and the radial step of the biasing member cover 56. The biasing member 60 is thereby arranged to force the container cover 54 relative to the housing 48 towards the proximal direction 16.

The base unit 44 comprises an electric drive arrangement 62 and a switch 64. The drive arrangement 62 is configured to drive expulsion of medicament from the medicament container 36. The switch 64 is configured to activate the drive arrangement 62. The base unit 44 of this example also comprises a further switch (not visible) for detecting when the cassette 46 is connected to the base unit 44.

The drive arrangement 62 of this specific example comprises a battery 66, a printed circuit board (PCB) 68, an electric motor 70 powered by the battery 66, a chain drive having a roller chain 72 and a sprocket 74, and a plunger 76. The sprocket 74 is rotationally driven by the electric motor 70 via a transmission (not denoted).

The switch 64 of this example comprises a lever tiltable between a passive state, as shown in FIGS. 6 and 7, and an active state. The switch 64 is arranged on the PCB 68. In the illustrated passive state, the lever is raised from the PCB 68. In the active state, the lever is lowered to the PCB 68.

The container cover 54 comprises a switch activation part 78. The switch activation part 78 is arranged to activate the switch 64 in response to an axial movement of the container cover 54 in the distal direction 18. In this example, the switch activation part 78 is arranged to push the switch 64 from the passive state to the active state by distal movement of the container cover 54.

The switch activation part 78 of this example is an integral part of the container cover 54. The switch activation part 78 is arranged at a distal end of the container cover 54.

Figure 9:
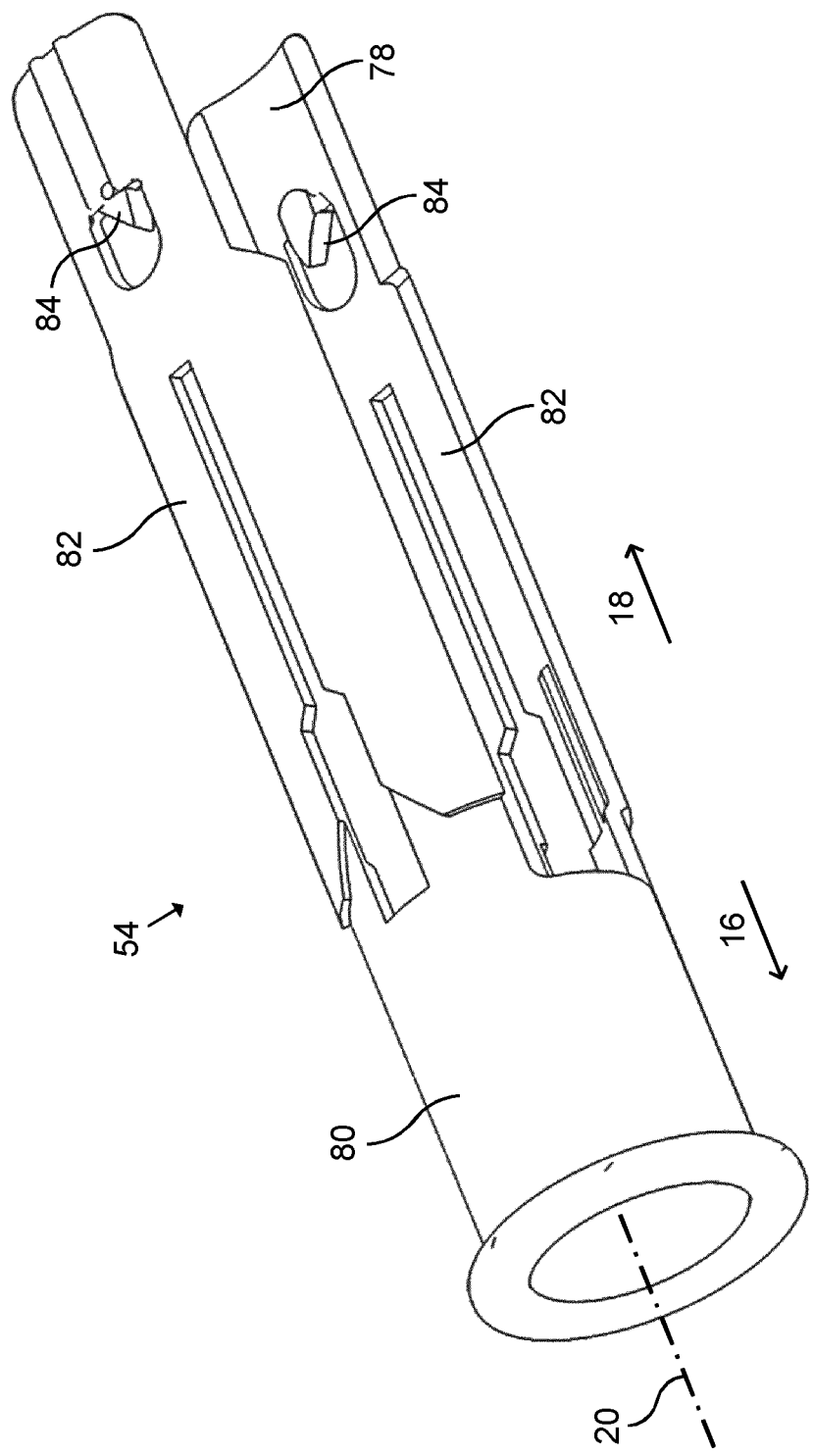
FIG. 9 schematically represents a perspective view of a container cover of the medicament delivery device.

FIG. 9 schematically represents a perspective view of the container cover 54. The container cover 54 comprises a cover body 80 and two cover arms 82 extending distally from the cover body 80 substantially parallel with the longitudinal axis 20. The cover arms 82 are oppositely arranged with respect to the longitudinal axis 20. In FIG. 9, the switch activation part 78 is shown more clearly. Although the container cover 54 of this example comprises two cover arms 82, the container cover 54 may alternatively comprise only one cover arm 82, or more than two cover arms 82.

The container cover 54 further comprises two cover structures 84. Each cover structure 84 is arranged in a distal region of a cover arm 82. In this example, each cover structure 84 is a radially inwardly protruding pin.

Figure 10:
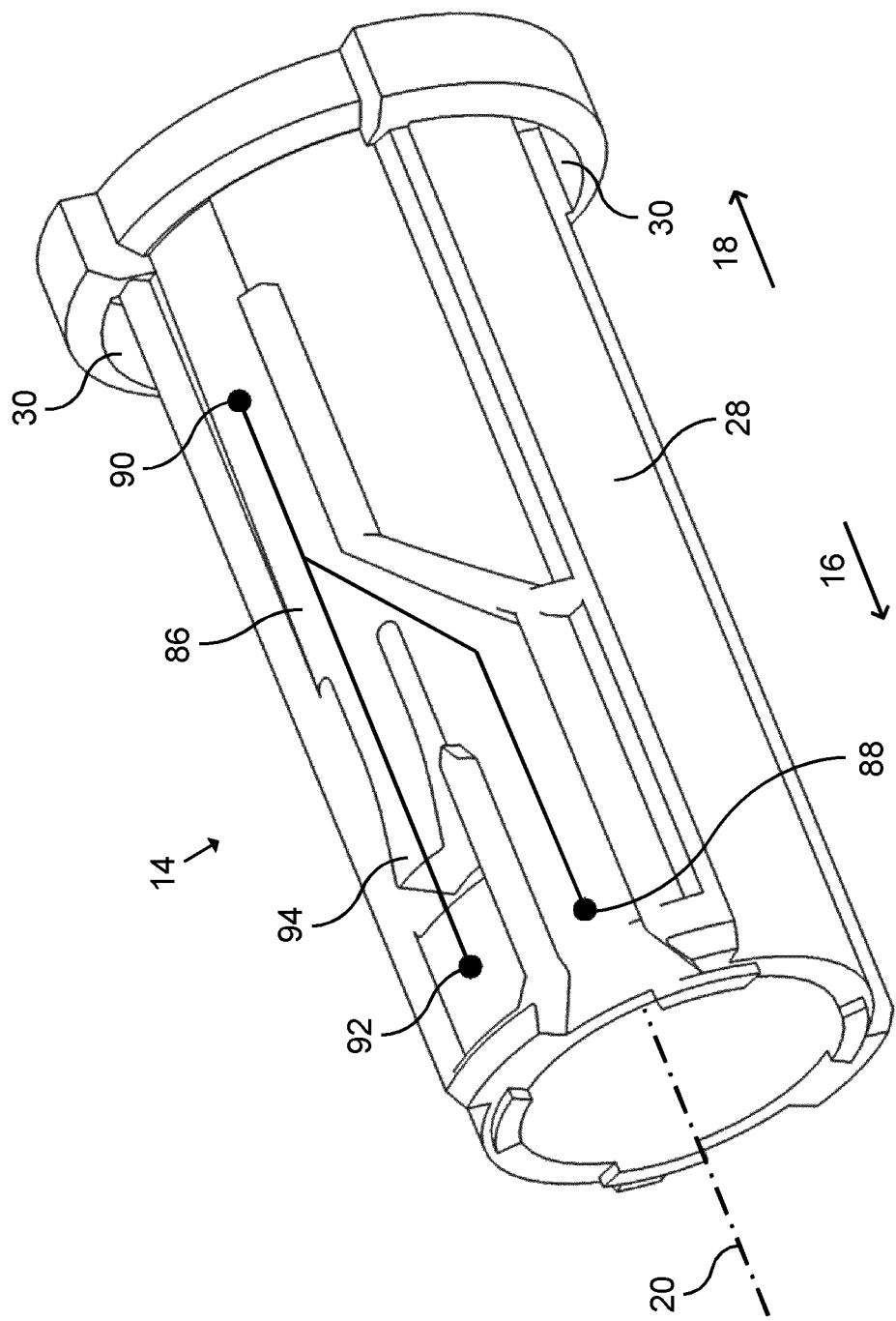
FIG. 10 schematically represents a further perspective view of the rotator of the assembly.

FIG. 10 schematically represents a further perspective view of the rotator 14. The rotator 14 comprises two engageable rotator structures 86 (only one is visible in FIG. 10). The rotator structures 86 are oppositely arranged with respect to the longitudinal axis 20. Each rotator structure 86 is configured to be engaged by one of the cover structures 84.

Each rotator structure 86 in this example is a track configured to be followed by one of the cover structures 84. The rotator structure 86 comprises a first position 88, a second position 90 and a third position 92.

The rotator structure 86 further comprises a flexible rotator arm 94. The rotator arm 94 is arranged along the track between the second position 90 and the third position 92.

When the cover structure 84 engages the first position 88 of the rotator structure 86, the proximal end 40 of the medicament container 36 is covered by the container cover 54. When the container cover 54 is pushed distally, the cover structure 84 moves from the first position 88 to the second position 90. During this movement, the rotator 14 rotates about the longitudinal axis 20.

When the cover structure 84 engages the second position 90 of the rotator structure 86, the proximal end 40 of the medicament container 36 is exposed. The container cover 54 may then move proximally, by means of the force from the biasing member 60, from the second position 90 to the third position 92. During this movement, the rotator arm 94 is deflected radially inwards. When the cover structure 84 has passed over the rotator arm 94, the rotator arm 94 returns to its neutral state (as illustrated in FIG. 10) and thereby prevents the cover structure 84 from moving away from the third position 92. Thereby, the container cover 54 is locked.

Figure 11:
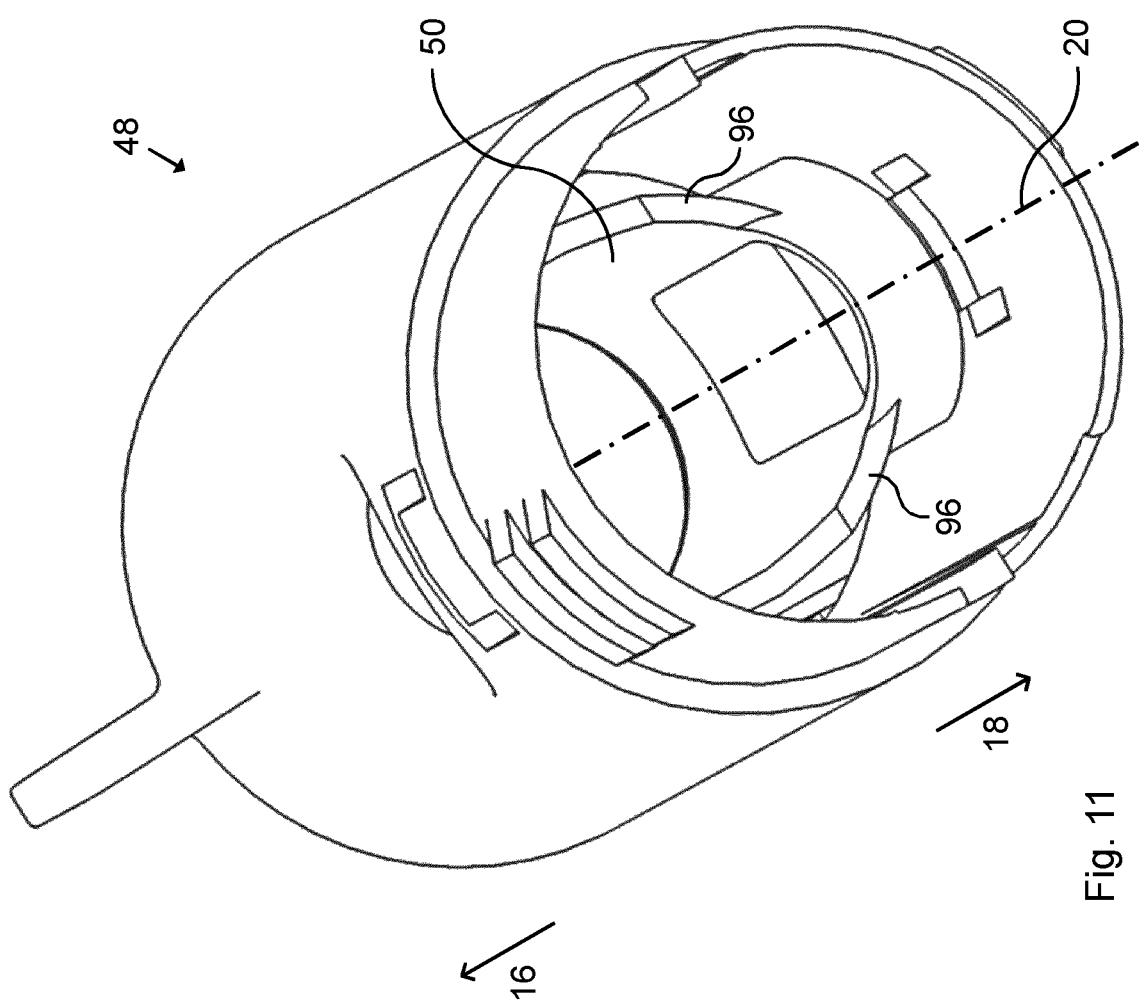
FIG. 11 schematically represents a perspective view of a housing of the cassette.

FIG. 11 schematically represents a perspective view of the housing 48. The housing 48 comprises housing guide surfaces 96 arranged on the inner part 50. The housing guide surfaces 96 extend radially and at an angle to the longitudinal axis 20. The housing guide surfaces 96 are arranged to cooperate with the carrier guide surfaces 34 of the container carrier 12 during insertion of the assembly 10 into the housing 48 such that the container carrier 12 becomes rotationally locked to the housing 48. The carrier guide surfaces 34 and the housing guide surfaces 96 thus form one example of a guide arrangement as described herein.

In the following, one example of operation of the medicament delivery device 42 will be described. The user connects the cassette 46 containing a medicament container 36 to the base unit 44. The user may then turn on the power of the base unit 44. A further switch of the base unit 44 senses that the cassette 46 is connected to the base unit 44.

The user then brings the medicament delivery device 42 towards a dose delivery site such that the container cover 54 contacts the dose delivery site. The medicament delivery device 42 is then pressed against the dose delivery site. This causes the container cover 54 to move distally relative to the remainder of the medicament delivery device 42 and the switch activation part 78 to activate the switch 64. A dose delivery function is thereby activated only by pressing the medicament delivery device 42 against a dose delivery site.

The base unit 44 may comprise an LED (not shown) indicating initiation of medicament delivery. A sound and/or tactile signal may be issued once the medicament delivery is completed.

When the medicament delivery device 42 is removed from the dose delivery site, the biasing member 60 forces the container cover 54 proximally to again to cover the proximal end 40 of the medicament container 36. This also causes the cover structure 84 to engage the third position 92 of the rotator structure 86 such that the container cover 54 becomes locked. The switch 64 is released when container cover 54 has moved proximally again. This causes the drive arrangement 62 to move back to the initial state including retraction of the plunger 76. The cassette 46 is then disconnected from the base unit 44 and discarded. A further cassette 46 may then be connected to the base unit 44 again for a further dose delivery.

While the present disclosure has been described with reference to exemplary embodiments, it will be appreciated that the present disclosure is not limited to what has been described above. For example, it will be appreciated that the dimensions of the parts may be varied as needed. Accordingly, it is intended that the present disclosure may be limited only by the scope of the claims appended hereto.

The invention claimed is:

1. An assembly for receiving a medicament container, the assembly comprising:
 a container carrier extending along a longitudinal axis, the container carrier comprising a carrier body, and a flexible carrier arm extending from the carrier body substantially parallel with the longitudinal axis; and
 a rotator comprising a hollow rotator body and at least one through hole which extends substantially parallel with the longitudinal axis; wherein the through hole is arranged radially with respect to the longitudinal axis outside the rotator body;
 wherein the container carrier is arranged to receive the rotator such that the carrier arm extends through the through hole,
 wherein the rotator is arranged to rotate about the longitudinal axis and relative to the container carrier, and
 wherein the carrier arm comprises an engaging arm structure arranged to resiliently engage a flange of the medicament container to thereby lock the medicament container along the longitudinal axis when the rotator is received by the container carrier and the medicament container is received by the assembly.

2. The assembly according to claim 1, wherein each engaging arm structure has a recess.

3. A cassette for receiving a medicament container, the cassette comprising the assembly according to claim 1.

4. The cassette according to claim 3, further comprising:
a housing configured to receive the assembly;
a container cover for covering a proximal end of the medicament container when received in the assembly; and
a biasing member arranged to bias the container cover relative to the housing in a proximal direction.

5. The cassette according to claim 4, wherein the container cover is axially movable and non-rotatable relative to the housing.

6. The cassette according to claim 4, wherein the rotator is rotatable relative to the container cover.

7. The cassette according to claim 6, wherein the rotator comprises an engageable rotator structure, wherein the container cover comprises a cover structure engaging the rotator structure, wherein the cover structure is arranged to move from a first position of the rotator structure to a second position of the rotator structure in response to an axial movement of the container cover in a distal direction, and wherein the cover structure is arranged to move from the second position to a third position of the rotator structure in response to an axial movement of the container cover in the proximal direction.

8. The cassette according to claim 7, wherein the cover structure and the rotator structure are arranged such that the container cover becomes locked to the rotator when the cover structure engages the third position of the rotator structure.

9. The cassette according to claim 7, wherein the rotator structure comprises a flexible rotator arm arranged between the second position and the third position, wherein the rotator arm is arranged to deflect from a neutral position when the cover structure moves along the rotator structure from the second position to the third position, and wherein the rotator arm is arranged to return to the neutral position when the cover structure has passed the rotator arm.

10. The cassette according to claim 4, further comprising a guide arrangement configured to guide the container carrier about the longitudinal axis with respect to the housing when the container carrier is inserted into the housing.

11. A medicament delivery device comprising the cassette according to claim 3.

12. The medicament delivery device according to claim 11, further comprising:
a base unit having an electric drive arrangement and a switch for activating the drive arrangement;
wherein the cassette is detachably attachable to the base unit, and comprises a switch activation part arranged to activate the switch in response to an axial movement of the container cover in a distal direction when the cassette is attached to the base unit; and
wherein the drive arrangement is arranged to drive expulsion of medicament from the medicament container when the cassette is attached to the base unit and the switch is activated.

13. The medicament delivery device according to claim 12, wherein the switch activation part is fixed with respect to the container cover.

14. The medicament delivery device according to claim 12, wherein the switch activation part is arranged to move in the distal direction in response to the movement of the container cover in the distal direction in order to activate the switch.

15. An assembly for receiving a medicament container, the assembly comprising:
a container carrier extending along a longitudinal axis and comprising a carrier body, and two flexible carrier arms extending from the carrier body substantially parallel with the longitudinal axis; and
a rotator comprising a hollow rotator body and two through holes each of which extends substantially parallel with the longitudinal axis, where the through holes are arranged radially with respect to the longitudinal axis outside the rotator body,
wherein the rotator is positioned between the two flexible carrier arms such that each carrier arm extends through one of the through holes, and
wherein the rotator rotates relative to the carrier arms and about the longitudinal axis such that carrier arms remain in the through holes.

16. The assembly according to claim 15, wherein a distal end of each carrier arm extends outward of a distal end of the through hole and has a recess on an inner surface that resiliently engages an outside radial edge of a flange of the medicament container to lock the medicament container axially relative to the rotator.

17. The assembly according to claim 15, wherein the proximal end of the container carrier is C-shaped and radially flexible.

18. The assembly according to claim 15, wherein container carrier further comprises one or more carrier guide surfaces that extend radially outward from an outer surface and have an angled surface relative to the longitudinal axis.

19. The assembly according to claim 18, wherein the one or more carrier guide surfaces slidably engage housing guide surfaces on an inside surface of a housing enclosing the assembly when the assembly is inserted into the housing such that the container carrier becomes rotationally locked to the housing.

* * * * *